(12) United States Patent
Varanasi et al.

(10) Patent No.: US 8,292,196 B2
(45) Date of Patent: Oct. 23, 2012

(54) METHODS FOR REDUCING SEEPAGE FROM WICK-BASED CONTROLLED RELEASE DEVICES, AND WICK-BASED DEVICES HAVING REDUCED SEEPAGE

(75) Inventors: Padma Prabodh Varanasi, Racine, WI (US); Joel E. Adair, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 1043 days.

(21) Appl. No.: 11/120,475

(22) Filed: May 3, 2005

(65) Prior Publication Data

US 2005/0247802 A1      Nov. 10, 2005

Related U.S. Application Data

(60) Provisional application No. 60/568,694, filed on May 7, 2004.

(51) Int. Cl.
| | | |
|---|---|---|
| A24F 25/00 | (2006.01) | |
| A01G 27/00 | (2006.01) | |
| B05B 9/00 | (2006.01) | |
| A62C 5/00 | (2006.01) | |

(52) U.S. Cl. ............ 239/44; 239/47; 239/145; 239/326; 239/398

(58) Field of Classification Search ............ 239/44, 239/326, 145, 398, 34, 303–306, 53, 47, 239/35–43, 45, 46, 48–52, 54–60

See application file for complete search history.

(56) References Cited

U.S. PATENT DOCUMENTS

| | | | |
|---|---|---|---|
| 2,246,008 A * | 6/1941 | Rooch | 239/42 |
| 2,987,261 A * | 6/1961 | McCuiston et al. | 239/304 |
| 3,633,881 A | 1/1972 | Yurdin | |
| 3,674,567 A * | 7/1972 | Bradley | 429/418 |
| 4,286,754 A | 9/1981 | Jones | |
| 4,323,193 A | 4/1982 | Compton et al. | |
| 4,413,779 A | 11/1983 | Santini | |
| 4,419,326 A | 12/1983 | Santini | |
| 4,663,315 A | 5/1987 | Hasegawa et al. | |
| 4,732,321 A * | 3/1988 | Dolan | 239/45 |
| 4,739,928 A * | 4/1988 | O'Neil | 239/45 |
| 4,898,328 A | 2/1990 | Fox et al. | |
| 4,948,047 A * | 8/1990 | Zembrodt | 239/34 |
| 4,968,487 A | 11/1990 | Yamamoto et al. | |
| 4,983,578 A * | 1/1991 | Cashman et al. | 512/3 |
| 5,047,234 A * | 9/1991 | Dickerson et al. | 424/76.2 |
| 5,081,104 A | 1/1992 | Orson, Sr. | |
| 5,832,648 A * | 11/1998 | Malone | 43/1 |
| 5,906,298 A * | 5/1999 | Ward | 222/175 |
| 5,932,204 A | 8/1999 | Joshi | |

(Continued)

FOREIGN PATENT DOCUMENTS

WO      WO 02/30220 A1      4/2002

(Continued)

*Primary Examiner* — Len Tran
*Assistant Examiner* — Steven M Cernoch

(57) ABSTRACT

Methods and devices include having a container (1) for holding a liquid with a viscosity μ, and a porous wick (5) with an average pore size of at least about 4 microns to about 50 microns and a porosity ϵ between about 0.20 to about 0.75, and having a length L and a total exposed surface area A exposed to the ambient air. The viscosity of the liquid and the dimensions of the wick are such that a quantity A/μL is in a range of about $4 \times 10^{-4}$ to about 18 cm/poise.

17 Claims, 8 Drawing Sheets

U.S. PATENT DOCUMENTS

| | | | |
|---|---|---|---|
| 5,947,379 A * | 9/1999 | Freeman | 239/52 |
| 6,217,315 B1 * | 4/2001 | Mifune et al. | 431/321 |
| 6,386,195 B1 * | 5/2002 | Coffee | 128/200.14 |
| 6,386,462 B1 | 5/2002 | Martens, III | |
| 6,435,423 B2 | 8/2002 | Hurry et al. | |
| 6,729,552 B1 * | 5/2004 | McEwen et al. | 239/49 |
| 6,820,363 B1 * | 11/2004 | Averette, Jr. | 43/1 |
| 7,007,863 B2 * | 3/2006 | Kotary et al. | 239/44 |
| 7,252,244 B2 * | 8/2007 | Martens, III | 239/44 |
| 7,419,102 B2 * | 9/2008 | Harris, Jr. | 239/48 |
| 2001/0030243 A1 | 10/2001 | Hurry et al. | |
| 2002/0045684 A1 * | 4/2002 | Bacher et al. | 524/4 |
| 2002/0136886 A1 * | 9/2002 | He et al. | 428/313.5 |
| 2003/0024997 A1 * | 2/2003 | Welch et al. | 239/53 |
| 2004/0055678 A1 * | 3/2004 | Hales et al. | 149/109.6 |
| 2004/0065749 A1 * | 4/2004 | Kotary et al. | 239/44 |
| 2004/0065750 A1 * | 4/2004 | Kotary et al. | 239/44 |
| 2004/0074982 A1 * | 4/2004 | Kotary et al. | 239/44 |
| 2004/0182949 A1 * | 9/2004 | Duston et al. | 239/44 |
| 2004/0262419 A1 * | 12/2004 | Kotary et al. | 239/44 |

FOREIGN PATENT DOCUMENTS

WO    WO 2004006968 A1 *    1/2004

* cited by examiner

METHODS FOR REDUCING SEEPAGE FROM WICK-BASED CONTROLLED RELEASE DEVICES, AND WICK-BASED DEVICES HAVING REDUCED SEEPAGE

This application claims the benefit of U.S. Provisional Application No. 60/568,694 filed on May 7, 2004.

BACKGROUND OF THE INVENTION

I. Field of the Invention

This invention relates to wick-based controlled release devices. In particular, the invention relates to methods for reducing seepage from a wick-based controlled release device for transporting liquids, such as fragrances or insect repellants, from a reservoir to a surface exposed to the ambient air. The invention also relates to a wick-based controlled release device having reduced seepage.

II. Description of the Related Art and Problem to Be Solved

Devices that release vapors into the ambient air are well-known in the art. Generally, the purpose of these devices is to deodorize, disinfect, or impart a desired fragrance to the ambient air, or to distribute toxins into the air to kill or to repel unwanted pests, such as insects.

Several methods have been employed to dispense vapors into the air. For example, aerosol containers have been used to eject vapors into the air upon the activation of a trigger by a user. Other methods, however, utilize the evaporative properties of liquids, or of other vaporizable materials, to cause vapors with desired properties to be distributed into the ambient air. One such evaporative method utilizes a wick to deliver a vaporizable liquid from a reservoir to a surface exposed to the ambient air. From the exposed surface, the liquid is vaporized and dispersed into the ambient air. The exposed surface may be either the surface of the wick or the surface of another body in fluid communication with the wick.

Because wick-based controlled release devices have a surface exposed to the ambient air, as well as a path for vaporizable liquid to reach the exposed surface, unwanted seepage (leakage) of the liquid can be a problem. For instance, seepage of the liquid can occur when the wick-based devices are accidentally overturned, such as during packaging, shipping, or use by the consumer. The seepage can occur through the wick itself, as well as through any opening in the wick-based device, such as a vent hole provided to prevent vacuum formation in the liquid reservoir. Therefore, a need exists, in the design of wick-based controlled release devices, to reduce the amount of seepage of liquid from such devices.

It has previously been suggested that pore size and/or porosity of a wick may be selected to reduce seepage. For example, U.S. Pat. No. 4,968,487 discloses that, in order to prevent leakage from a wick in a wick-based device and to ensure that the liquid in the device transpires stably and effectively, the porosity of the wick should be restricted to a range of 25 to 40 percent. U.S. Patent Publication No. 2002/0136886 A1 discloses that a pore size of less than about 250 microns and a porosity of less than about 60 percent achieves effective control of liquid delivery with an additional benefit of reducing or preventing leakage.

It is also known in the art that the properties and evaporation rate of liquids in wick-based devices may be advantageously selected or controlled.

For example, U.S. Pat. No. 4,663,315 teaches a vaporizable composition including an organic solvent, an active ingredient, and at least one compound selected from a group of compounds listed in the patent, such as 3,5-di-t-butyl-4-hydroxytoluene, 3-t-butyl-4-hydroxyanisole, and mercaptobenzimidazole. According to the '315 patent, the composition provides efficient evaporation of the active ingredient and is capable of being drawn up a reservoir by an absorbing body, such as a wick, without clogging the absorbing body.

Further, U.S. Pat. No. 5,081,104 discloses that the solubility and evaporation rates of volatile fragrances such as perfumes are improved by the addition of 3-methyl-3-methoxy butanol or an ester thereof. Evaporation-rate-modifying solvents may be added to the composition taught by the patent, but addition of a surfactant is said to be undesirable because the surfactant would tend to clog a wick and block surface evaporation. The composition disclosed in the '104 patent may be in the form of a paste or a gel, obtained by the addition of thickeners, such as carboxymethyl cellulose.

We believe, however, that there is still room for improvement in controlling the seepage of liquid in wick-based controlled release devices.

SUMMARY OF THE INVENTION

We have determined that seepage of liquid from the wick (and, if present, the vent hole) of a wick-based device may be minimized, without excessively reducing the release rate of the liquid, by adjusting the viscosity of the liquid in combination with adjusting the exposed surface area of the wick.

In one aspect, this invention provides a method for reducing the seepage of liquid from a wick-based device having a container for holding a liquid with a viscosity $\mu$, and a porous wick. The porous wick preferably has an average pore size of at least about 4 microns at the lower end. More preferably, the wick has an average pore size of about 4 microns, at least, to about 50 microns at the upper end, and a porosity between about 0.20 to about 0.75, and has a length L and a total exposed surface area A exposed to the ambient air. The method includes a step of adjusting at least one of the viscosity $\mu$ of the liquid, the length L of the wick, and the total exposed surface area A of the wick, such that a quantity $A/\mu L$ is in a range of about $4 \times 10^{-4}$ to about 18 cm/poise.

The invention provides, in another aspect, a wick-based device including a container for holding a liquid having a viscosity $\mu$, and a porous wick with an average pore size of at least about 4 microns to about 50 microns and a porosity between about 0.20 to about 0.75, and having a length L and a total exposed surface area A exposed to the ambient air. The container has an opening at a top surface of the container, and the wick extends through the opening in the container such that an upper region of the wick is exposed to the ambient air and a lower region of the wick is in contact with the liquid to be held by the container. In the device, the viscosity of the liquid and the dimensions of the wick are such that a quantity $A/\mu L$ is in a range of about $4 \times 10^{-4}$ to about 18 cm/poise.

In a third aspect, the invention provides a wick-based device including a liquid having a viscosity $\mu$, a container for holding the liquid, and a porous wick with an average pore size of at least about 4 microns to about 50 microns and a porosity between about 0.20 to about 0.75, and having a length L and a total exposed surface area A exposed to the ambient air. The container has an opening at a top surface of the container, and the wick extends through the opening in the container such that an upper region of the wick is exposed to the ambient air and a lower region of the wick is in contact with the liquid held by the container. The viscosity of the liquid and the dimensions of the wick are such that a quantity $A/\mu L$ is in a range of about $4 \times 10^{-4}$ to about 18 cm/poise.

In a fourth aspect, the invention provides a method for reducing seepage of liquid from a wick-based device having a porous wick, the wick having pores with pore walls, and a container for holding a first liquid having a first viscosity. The method includes the steps of providing a second liquid having a second viscosity greater than the first viscosity, the second liquid being able to absorb into the pore walls in the wick and decrease the effective size of the pore, and applying the second liquid to the wick such that at least a part of the wick is saturated with the second liquid.

In a fifth aspect, the invention provides a wick-based device including a container for holding a first liquid having a first viscosity, and a porous wick, having pores with pore walls, which is at least partially saturated with a second liquid having a second viscosity greater than the first viscosity. The container has an opening at a top surface of the container, and the wick extends through the opening in the container such that an upper region of the wick is exposed to the ambient air and a lower region of the wick is in contact with the first liquid. In the device, the second liquid is absorbed into the pore walls in the wick and decreases the effective size of the pores.

In a sixth aspect, the invention provides a wick-based device including a first liquid having a first viscosity, a container for holding the first liquid, a porous wick having pores with pore walls, and a second liquid, with a second viscosity greater than the first viscosity, absorbed into the pore walls in at least a part of the wick in such a manner that the effective size of the pores is decreased. In the device, the container has an opening at a top surface of the container, and the wick extends through the opening in the container such that an upper region of the wick is exposed to the ambient air and a lower region of the wick is in contact with the first liquid.

DETAILED DESCRIPTION OF THE INVENTION

I. Description of the Wick-Based Device

In general, a wick-based, controlled-release device includes a container and a wick. According to the invention, the container can be formed in a variety of shapes, and any wick that is porous can be used.

Figure 1:
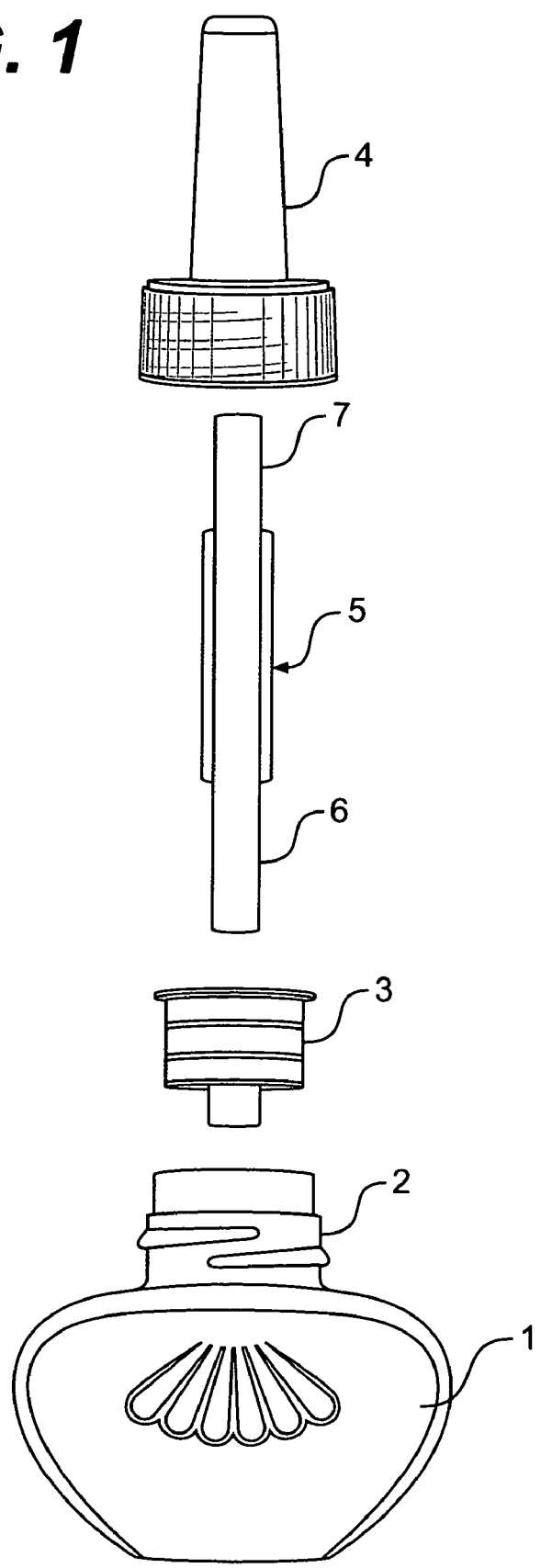
FIG. 1 is an exploded view of a wick-based, controlled-release device according to a preferred embodiment of the invention.

In the example shown in FIG. 1, the container is a bottle 1 of conventional shape. A porous wick 5 is shaped so that it fits snugly into a neck 2 of the bottle 1. The wick 5 is long enough so that its lower portion 6 comes into contact with liquid in the bottle 1 and its upper portion 7 is exposed to the ambient air. (The level of the liquid in the bottle 1 is not shown in FIG. 1.) It is preferable to use a neck closure 3, such as that shown in FIG. 1, to hold the wick 5 in place.

As the liquid is drawn from the bottle 1 and transported up the porous wick 5, a vacuum is created in the head-space of the bottle 1. The formation of such a vacuum can decrease the rate at which the liquid is drawn up the wick 5. In order to avoid the formation of the vacuum, it is often preferable to form a small hole in the vicinity of the head-space of the bottle 1. For example, the neck closure 3 or the neck 2 of the bottle 1 may be formed with a vent hole (not shown).

In addition, the neck 2 of the bottle 1 can be shaped so that a cover 4 can be securely fastened over the wick 5 and the neck closure 3. For example, the neck 2 may be threaded so that the cover 4 can be screwed on top of the bottle 1 when the device is not in use.

The bottle 1 and the neck closure 3 can be made of any suitable material that is leak-proof. The size of the opening in the bottle 1 and the size of the neck closure 3 are dependent upon each other and upon the size of the wick 5 that is to be used with the device.

Figure 2:
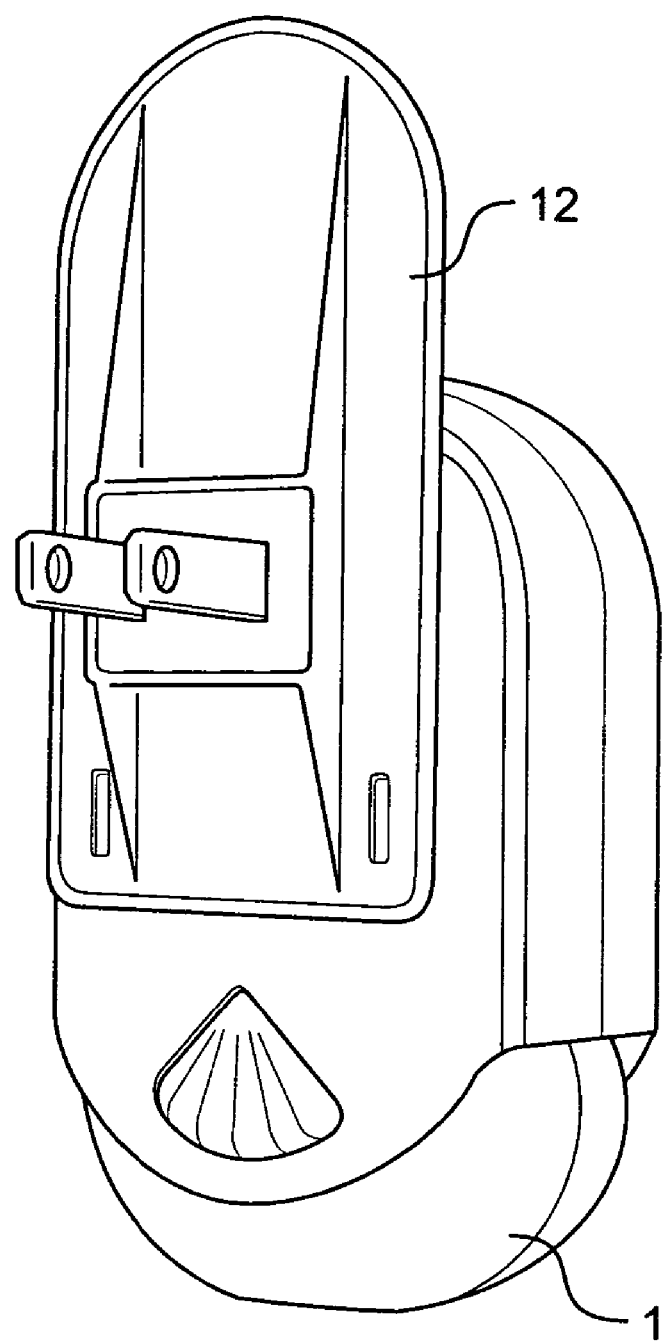
FIG. 2 is a view of the wick-based device of FIG. 1 being utilized in conjunction with an optional electric plug-in heater.

The wick-based device of FIG. 1 can be combined with an electric heater, such as the electric heater 12 shown in FIG. 2. In addition, U.S. Pat. No. 5,647,053, assigned to the assignee of this application, and which is incorporated in its entirety into this description by reference, describes a suitable electric plug-in heater. The wick-based device can also be combined with a battery-powered fan (not shown). Although not required, it is preferable that the wick-based device of the invention be combined with the electric heater or the fan in a removable manner. For example, the device may be constructed so that the bottle 1 can be combined with the electric heater 12 in a snap-and-fit manner, resulting in the assembled device shown in FIG. 2.

Figure 3:
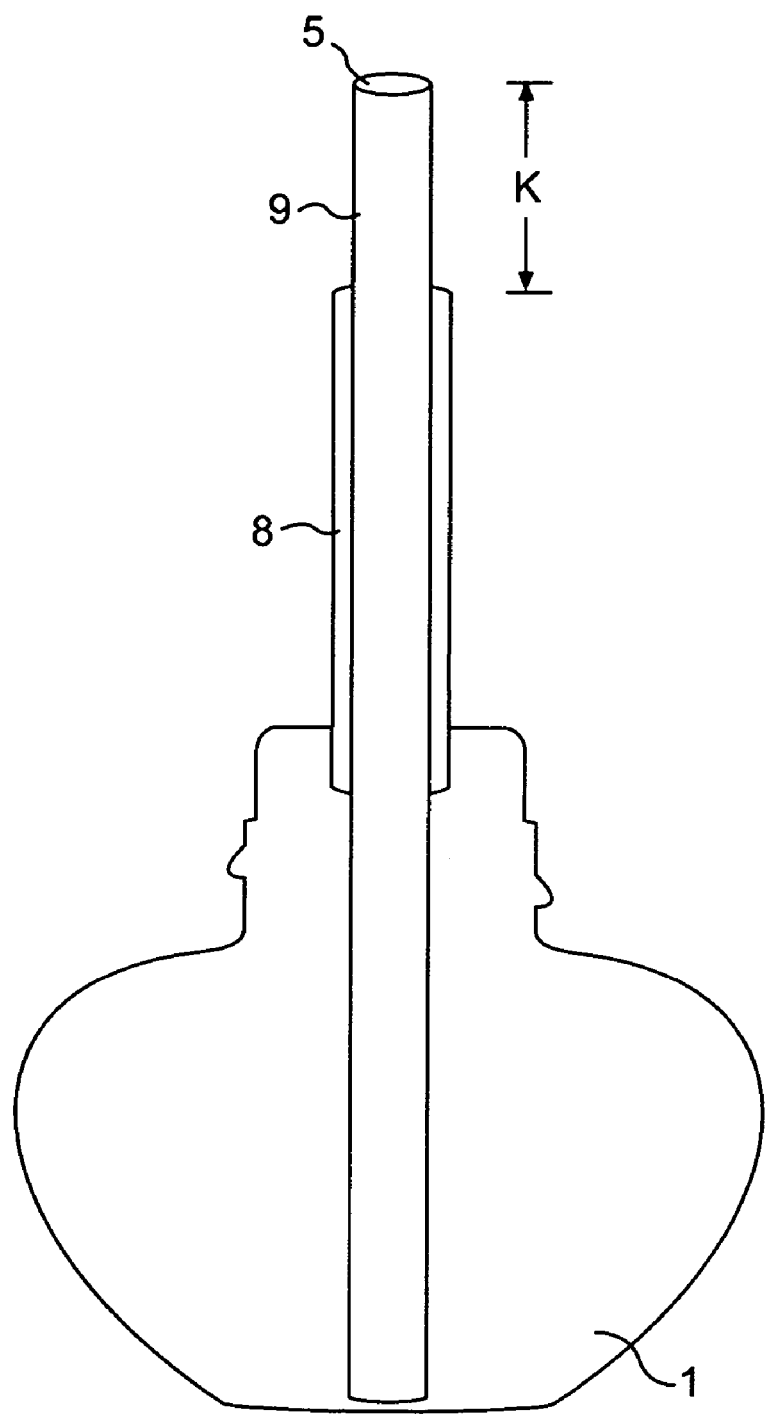
FIG. 3 is a schematic view of the wick-based device of FIG. 1, showing selected parts of the device.

FIG. 3 is a schematic view showing the wick 5 having been positioned in the bottle 1. The wick 5 has a wick sheath 8 that covers a portion of the wick 5 to prevent that portion from releasing a material by evaporation or by seeping. Exposed wick portion 9 is the upper portion of the wick 5 that is not covered by the wick sheath 8. The exposed wick portion 9 has a length K. (This length K is the "exposed length of the wick" referred to in exemplary experiments that are described later.)

Any wick that is porous may be suitable for use in embodiments of the invention. Further, a variety of materials can be used to make the wick. One example is high density polyethylene beads, which are sintered (formed into a coherent mass by heating, without melting) to create a wick with desired pore characteristics.

II. Seepage from Wick-Based Devices

Seepage of liquid can occur when a wick-based device is overturned. As stated, the seepage can occur through the wick, as well as through any opening in the device, such as a vent hole.

We have found that seepage of liquid in wick-based controlled release devices can be reduced by adjusting the viscosity of the liquid in combination with adjusting certain parameters of the wick. Advantageously, even though seepage is reduced, a desirable release rate of the liquid can be maintained. Therefore, the performance of the wick-based device is not sacrificed. We have also found that seepage can be reduced by first immersing the wick in a liquid with an adjusted viscosity. The purpose of the discussion in this section II is to explain the theory behind these findings in detail.

A. Factors Contributing to Seepage in Wick-Based Devices

To identify the factors that contribute to seepage from the wick of a wick-based device, the flow model within the wick must be examined.

Figure 4A:
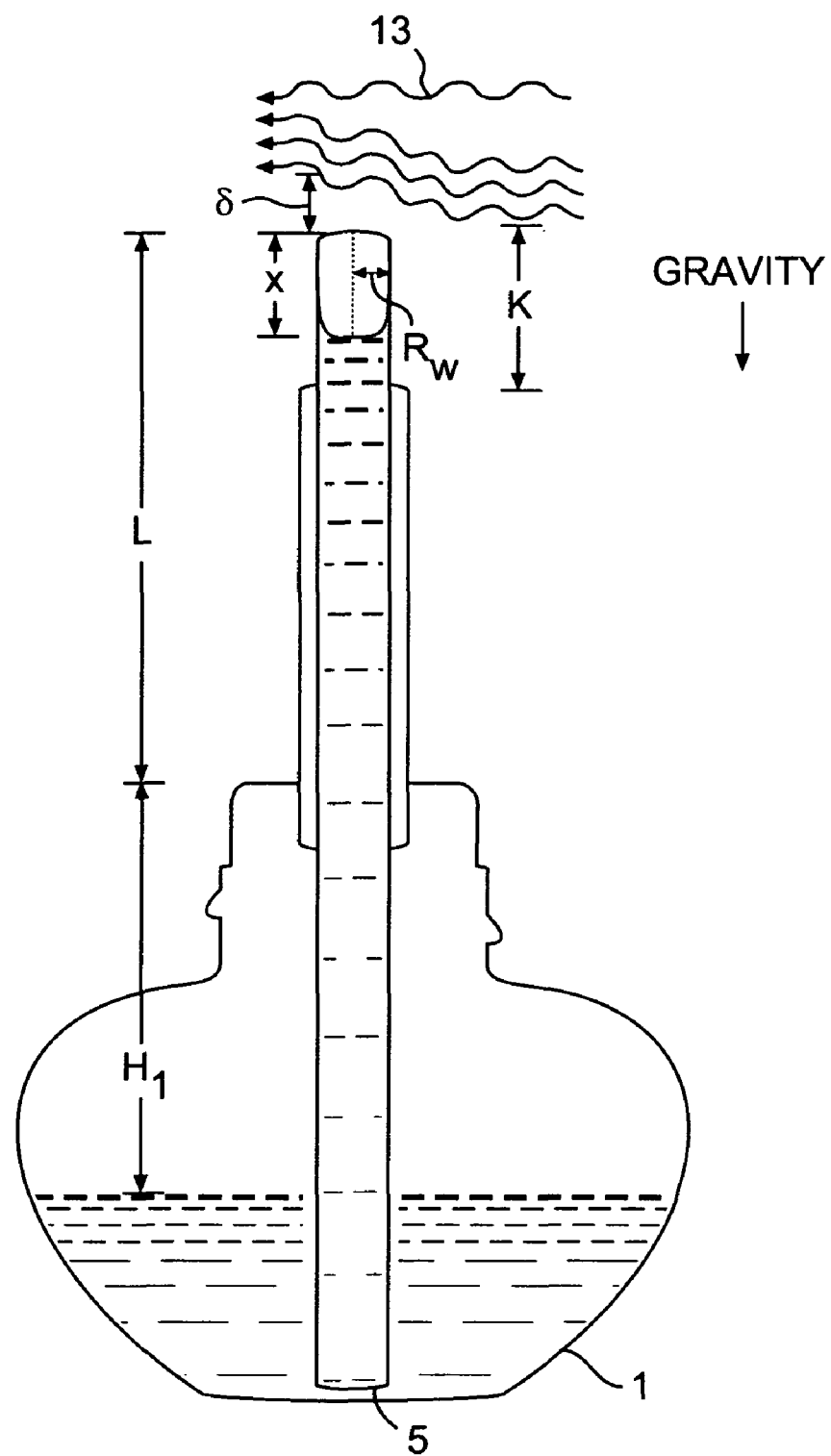
FIG. 4A is another schematic view of the wick-based device of FIG. 1, wherein the device contains liquid.
Figure 4B:
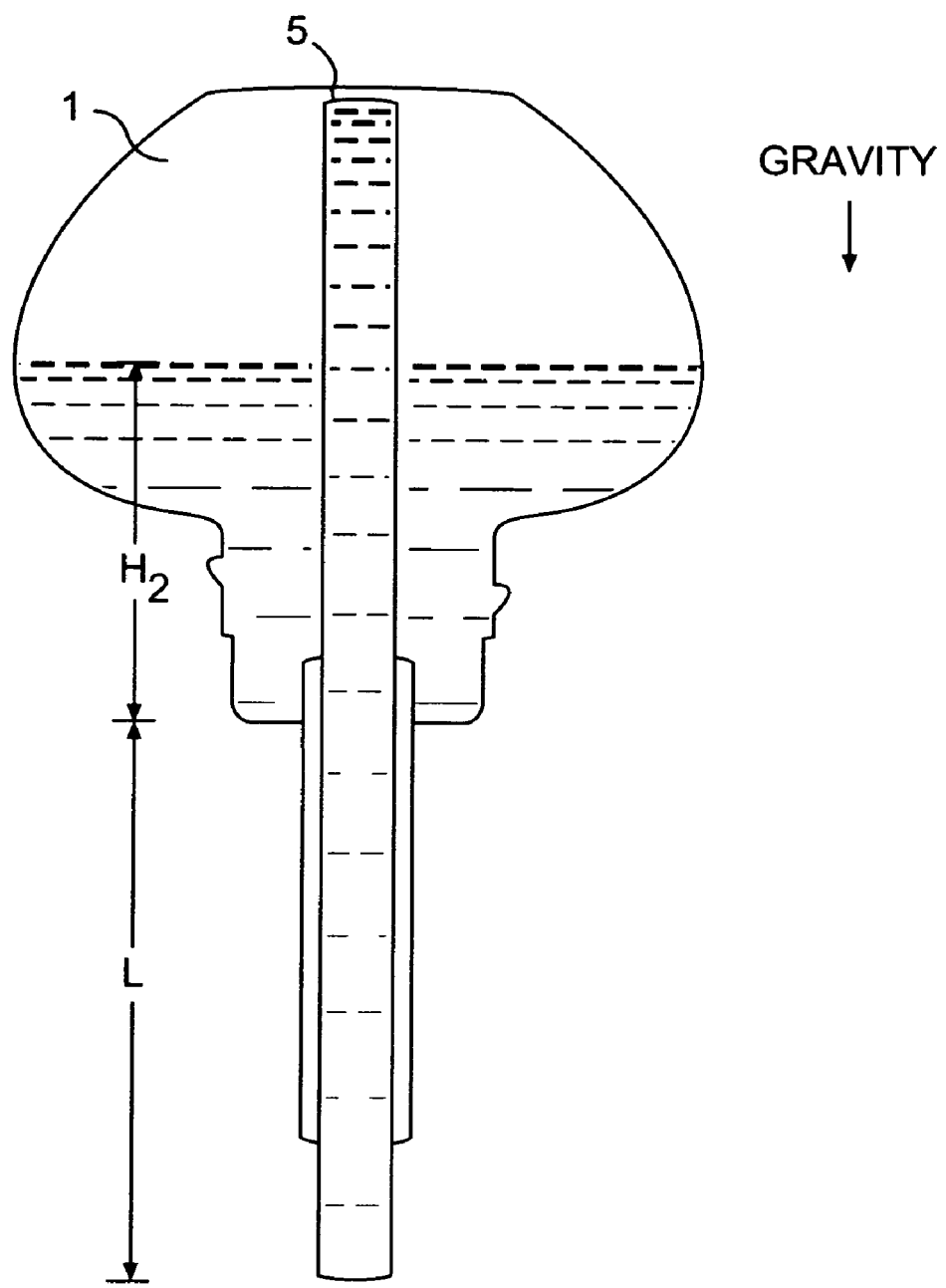
FIG. 4B shows the device of FIG. 4A in an upside-down state.

The wick has many wick pores, or small capillaries within the wick. Through capillary action, the wick draws in liquid and transports it to the surface of the wick (in FIG. 3, this would be the exposed wick portion 9). If the wick is considered as a system of many cylindrical tubes, then, following the Hagen-Poiseuille law for laminar flow in cylindrical tubes, the flow rate Q of liquid through the wick may be described by the equation $$Q = \frac{\Pi \Delta P}{8\left(\frac{\mu(L+H_2)}{R_p^2 \varepsilon R_w^2}\right)} \qquad \text{(Equation 1)}$$

where $\Pi$=pi,
$\Delta P$=pressure drop across the wick,
$R_p$=radius of pores in the wick,
$R_w$=radius of the wick (see FIG. 4A),
$\varepsilon$=porosity of the wick,
$\mu$=viscosity of the liquid that flows through the wick,
L=length of portion of the wick outside the bottle 1 (see FIGS. 4A and 4B), and
$H_2$=length of portion of the wick inside the bottle 1 that is submerged when the bottle 1 is turned upside-down (see FIG. 4B).

In Equation 1, the flow rate Q is directly proportional to the pressure drop across the wick.

Next, Ohm's Law is considered. Ohm's Law may be stated as $$I = \frac{V}{R} \qquad \text{(Equation 2a)}$$

or $$\text{current} = \frac{\text{driving force}}{\text{resistance}}. \qquad \text{(Equation 2b)}$$

Because the relationship between flow rate Q and pressure drop $\Delta P$ is analogous to the relationship between current and driving force, resistance to liquid flow through the wick may be written as $$\text{flow resistance} \propto \frac{\mu(L+H_2)}{\varepsilon R_p^2 R_w^2}. \qquad \text{(Equation 3)}$$

where, again,
$R_p$=radius of pores in the wick,
$R_w$=radius of the wick (see FIG. 4A),
$\varepsilon$=porosity of the wick,
$\mu$=viscosity of the liquid that flows through the wick,
L=length of portion of the wick outside the bottle 1 (see FIGS. 4A and 4B), and
$H_2$=length of portion of the wick inside the bottle 1 that is submerged when the bottle 1 is turned upside-down (see FIG. 4B).

To minimize the value of the flow rate Q, there must be either a decrease in the pressure drop across the wick or an increase in the flow resistance through the wick. Inspection of Equation 3 reveals that the flow resistance through the wick may be increased in the following ways:
1. By increasing the viscosity $\mu$ of the liquid.
2. By increasing the length L (and/or the length $H_2$).
3. By decreasing the wick porosity $\varepsilon$.
4. By decreasing the radius $R_p$ of the wick pores.
5. By decreasing the radius $R_w$ of the wick.

Initially, this discussion focuses mainly on the first option. However, as will be explained later in part D of this section, adjusting the viscosity of a liquid in which the wick is pre-immersed can also reduce seepage through option 4, by decreasing the radius $R_p$ of the wick pores.

By increasing the viscosity $\mu$ of the liquid in the device, the flow resistance through the wick (Equation 3) is increased, and the flow rate Q (Equation 1) is decreased. Since the flow rate Q is decreased, the amount of seepage of the liquid from the wick is reduced. Therefore, increasing the viscosity of the liquid decreases the seepage from the wick. (If the device holding the liquid has any vent holes, increasing the viscosity of the liquid will also reduce seepage of the liquid from the vent holes. This result is especially desirable given that vent holes can be a major source of seepage during the shipping process.)

B. Balancing Seepage Reduction Against Performance of the Wick-Based Device

Although increasing the viscosity $\mu$ of the liquid decreases the seepage from the wick, it also leads to a decrease in the wicking rate of the liquid, or the rate of flow at which liquid is transported against gravity through a wick due to surface tension forces. Wicking rate, in cubic centimeters per second, is determined according to the equation $$\text{rate}_{wicking} = \frac{\Pi \gamma R_p \varepsilon R_w^2}{4 \mu (L+H_1)} \qquad \text{(Equation 4)}$$

where $\gamma$ is the surface tension of the liquid (dyne/cm) and $H_1$ is the length of the portion of the wick inside the bottle 1 that is not submerged when the bottle 1 is right-side up (see FIG. 4A). The other variables are the same as those previously defined for Equation 1 and Equation 3, above.

As shown in Equation 4, viscosity is inversely proportional to the wicking rate. Therefore, although increasing the viscosity of the liquid will reduce the seepage of the liquid from the wick (and from any vent holes), it will also reduce the wicking rate, which can adversely affect the performance of the wick-based device. In particular, if the wicking rate is reduced so that it is smaller than the release rate of the liquid (that is, the rate at which the liquid is evaporated from the wick), the wicking rate will then become a limit on the release rate. In other words, in such a situation, the liquid can be dispersed into the air at a rate no faster than the wicking rate. Thus, there should be a balance between reduction of seepage, which is desirable, and excessive reduction in wicking rate (and therefore release rate), which is undesirable.

C. Compensating for Release-Rate Reduction

To compensate for the decrease in overall release rate resulting from increasing the viscosity of the liquid, certain parameters may be adjusted. The release rate of a liquid (or a portion of a liquid formulation, such as a fragrance portion) from a wick-based device is given by the equation $$\text{rate}_{release} = \frac{A_{exp} \varepsilon D}{(\delta + x)}\left(\frac{P_v}{RT} - C_o\right) \qquad \text{(Equation 5)}$$

where
$\delta$=thickness of the mass transport boundary layer (see FIG. 4A, in which reference number 13 denotes airflow),
x=distance between the top of the wick and the liquid front (see FIG. 4A),
$P_v$=vapor pressure of the liquid, $C_o$=concentration of vapor in the ambient air,
T=ambient temperature,
$A_{exp}$=total surface area of the wick exposed to the ambient air, or
$A_{exp}=\pi R^2+2\pi R_w K$ (where K=the exposed length of the wick, FIGS. 3 and 4A),
D=diffusion coefficient, and
R=universal gas constant.

As before,
$R_w$=radius of the wick, and
$\epsilon$=porosity of the wick.

As Equation 5 shows, ways to increase the overall release rate of the liquid from a wick-based controlled release device include the following:
1. Increasing the total surface area $A_{exp}$ of the wick exposed to ambient air.
2. Increasing the porosity $\epsilon$ of the wick.
3. Increasing the vapor pressure $P_v$ of the liquid.

The total surface area $A_{exp}$ of the wick exposed to ambient air may be increased, for example, by increasing the length K of the wick that is exposed to ambient air (FIGS. 3 and 4A) by lengthening the wick or by reducing the length of the sheath 8 of the wick (FIG. 3). However, increasing the exposed wick length, for example, can in turn cause an increase in seepage of the liquid, since some of the liquid would then flow through the surface of the wick (the surface of the exposed portion 9 in FIG. 3) at a rate faster than the rate of flow through the wick pores. This result underscores the balance of considerations that is necessary in determining a range of viscosity for a liquid in a wick-based controlled release device.

D. Adjusting Viscosity to Modify the Wick

As alluded to previously, adjusting the viscosity of a liquid in which the wick is pre-immersed can also reduce seepage by decreasing the radius $R_p$ of the wick pores in a wick. Suppose, for example, that one end of a wick is first immersed in a liquid with a suitably adjusted viscosity. (This end is opposite to the end that is placed, for example, in the bottle 1 of FIG. 1.) Molecules of the liquid will be absorbed in the walls of the wick pores, effectively reducing the pore size, i.e., the radius $R_p$. To review, by decreasing the radius $R_p$ of the wick pores, the flow resistance (Equation 3) is increased, and the flow rate Q (Equation 1) is decreased, resulting in decreased seepage.

Advantageously, according to this finding, the viscosity of all of the liquid in the liquid reservoir need not be adjusted. Only the viscosity of the liquid in which the wick is to be pre-immersed would be adjusted, which may be more economical. (Of course, the viscosity of both the immersing liquid and the liquid to be dispensed may be adjusted, if desired.) Further, according to this finding, it is possible essentially to achieve a wick of a different pore radius without having to manufacture or obtain a different wick. This also may be economical.

We have described pre-immersing one end of the wick in a liquid with a suitably adjusted viscosity, which liquid is capable of being absorbed in the walls of the wick pores, effectively reducing the pore size. However, this liquid can be applied to the wick by any conventional means, to any part of the wick that can absorb the liquid (including substantially the entire wick, depending on the length of the wick sheath), before, during, or after the wick is placed into a container holding liquid to be dispensed.

III. Selection of Thickener or Emulsifier

To reduce seepage by increasing the viscosity of the liquid in a wick-based controlled release device, a thickener can be added to and mixed with the liquid. We have found, in general, that thickeners are suitable if they satisfy the following criteria:

1. The thickener is soluble in the liquid.
2. The thickener does not react with the components of the liquid.
3. The thickener is able to wick up to the top of the wick.

Based on these criteria, we have found that ethyl cellulose, a polymeric thickener, is suitable for use in thickening liquid in wick-based devices. (Ethyl cellulose can also be used in preparing a thickened liquid to apply to the wick, to reduce the effective size of the wick pores.)

Other polymeric thickeners besides ethyl cellulose are also suitable. These include low molecular weight polyethylene, such as ACumist B-6, B-12, B-18, C-5, C-12, and C-18, all manufactured by Honeywell; ethylene homopolymers such as A-C6, A-C6A, A-C7, A-C7A, A-C8, A-C8A, A-C9, A-C9A, A-C9F, A-C15, A-C16, A-C617, A-C715, and A-C1702, all from Allied Signal; micronized polyethylene wax, such as ACumist A-6, A-45, B-9, C-9, C-30, and D-9, all from Honeywell; and styrene-butadiene-styrene triblock copolymers sold under the trade name Kraton by Shell Chemical Company. Of course, apart from polymeric thickeners, other thickeners meeting the above-mentioned criteria may also be used.

It is also possible to increase the viscosity of the liquid in the wick-based device (or to prepare a thickened liquid to apply to the wick, to reduce the effective size of the wick pores) by forming a water-in-oil type emulsion with an appropriate surface acting agent. For example, any emulsifier with a hydrophile-lipophile balance (HLB) value between 3 and 6, such as sorbitan monooleate (Span 80), may suitably be used to thicken the liquid, as long as the emulsifier does not react with the components of the liquid and as long as the emulsion can wick up the wick.

IV. Seepage Reduction Tests

The following non-limiting examples are presented to illustrate the principles and findings mentioned in sections II and III. We performed a first (multi-part) experiment exploring the idea of reducing seepage by thickening the viscosity of liquid to be dispensed from a wick-based device. In a second experiment, we explored the idea of reducing seepage by using thickened liquid to reduce the effective size of the wick pores. In both experiments, we used high density polyethylene wicks having a porosity of about 67%, an average pore radius of about 12 microns, and a wick radius of about 0.7 cm.

EXPERIMENT NO. 1

This first (multi-part) experiment will show that seepage of liquid can be significantly reduced by increasing the viscosity of the liquid and adjusting the exposed surface area of the wick. Despite the increase in viscosity, the release rate of the liquid is not sacrificed.

Example 1

First Seepage Test

Ethyl cellulose was tested as a possible candidate for increasing liquid viscosity in wick-based controlled release devices. The following mixtures of thickener agent and liquid were filled into Glade® Plug-In Scented Oil (PISO) bottles with vent holes and wicks with an exposed wick length of 0.25 inches (0.635 cm):
1) 0.5 wt % ethyl cellulose+pure fragrance
2) 1 wt % ethyl cellulose+pure fragrance
3) 1.5 wt % ethyl cellulose+pure fragrance Additional PISO bottles were also filled with pure fragrance, as a control.

Each filled bottle was weighed for initial mass and then rested on its side with the wick touching a corrugated surface. After twenty-four hours, each filled bottle was weighed again to find its final mass, and the amount of seepage (in grams/day) from each filled bottle was determined from the difference between its initial and final mass. Table 1 shows the seepage test results for pure fragrance, and mixtures of thickener agent and fragrance.

TABLE 1

Seepage Test Results for 0.25 inch (0.635 cm) Exposed Wick Length

| composition | Initial mass (g) | final mass (g) | Seepage (g/day) |
|---|---|---|---|
| pure fragrance | 30.354 | 27.783 | 2.571 |
| (control) | 30.212 | 27.38 | 2.832 |
|  | 29.145 | 26.63 | 2.515 |
|  | 29.611 | 27.44 | 2.171 |
|  |  |  | average: 2.52225 |
| 0.5% Ethyl Cellulose + | 30.47 | 29.644 | 0.826 |
| pure fragrance | 30.594 | 29.919 | 0.675 |
|  | 30.485 | 29.667 | 0.818 |
|  |  |  | average: 0.773 |
| 1% Ethyl Cellulose + | 30.489 | 30.24 | 0.249 |
| pure fragrance | 30.548 | 30.26 | 0.288 |
|  | 30.655 | 30.45 | 0.205 |
|  | 30.347 | 30.11 | 0.237 |
|  |  |  | average: 0.24475 |
| 1.5% Ethyl Cellulose + | 30.51 | 30.303 | 0.207 |
| pure fragrance | 30.459 | 30.233 | 0.226 |
|  | 30.564 | 30.437 | 0.127 |
|  |  |  | average: 0.187 |

Comparison of the average seepages for pure fragrance and the different thickened mixtures shows that the use of ethyl cellulose significantly diminished the amount of seepage from the wicks of the bottles.

Example 2

Evaporation Test

This test confirmed that increasing the total exposed area of the wick can compensate for a reduction in evaporation due to an increase in viscosity.

Two sets of PISO bottles with vent holes were prepared: one set in which the wick of each bottle had a 0.25 inch (0.635 cm) exposed wick length, and one set in which the wick of each bottle had a 0.8 inch (2.032 cm) exposed wick length.

The following mixtures of ethyl cellulose and pure fragrance were filled into the two sets of bottles:
1) 0.5 wt % ethyl cellulose+pure fragrance
2) 1 wt % ethyl cellulose+pure fragrance
3) 1.5 wt % ethyl cellulose+pure fragrance.

Additional bottles in both sets were also filled with pure fragrance, as a control.

Each filled bottle was weighed for initial mass and then was weighed again at the end of each of several consecutive twenty-four-hour intervals, in order to determine how much fragrance had evaporated each day from each bottle.

Table 2 shows data from this experiment for the set of PISO bottles with wicks having a 0.25 inch (0.635 cm) exposed wick length.

TABLE 2

Evaporation Test Results for 0.25 inch (0.635 cm) Exposed Wick Length

| elapsed time (days) | AVERAGE WEIGHT LOSS (grams/day) | | | |
|---|---|---|---|---|
|  | pure fragrance | 0.5% EC + pure fragrance | 1% EC + pure fragrance | 1.5% EC + pure fragrance |
| 1.0 | 0.70166 | 0.61801 | 0.53861 | 0.52846 |
| 2.1 | 0.59366 | 0.42365 | 0.39588 | 0.34322 |
| 5.0 | 0.48694 | 0.33426 | 0.23982 | 0.22638 |
| 6.0 | 0.52276 | 0.26503 | 0.22624 | 0.19459 |
| 7.0 | 0.46376 | 0.25877 | 0.22173 | 0.18385 |
| 8.0 | 0.38029 | 0.16586 | 0.14285 | 0.12304 |
| 9.0 | 0.41243 | 0.21404 | 0.19074 | 0.16723 |

Figure 5:
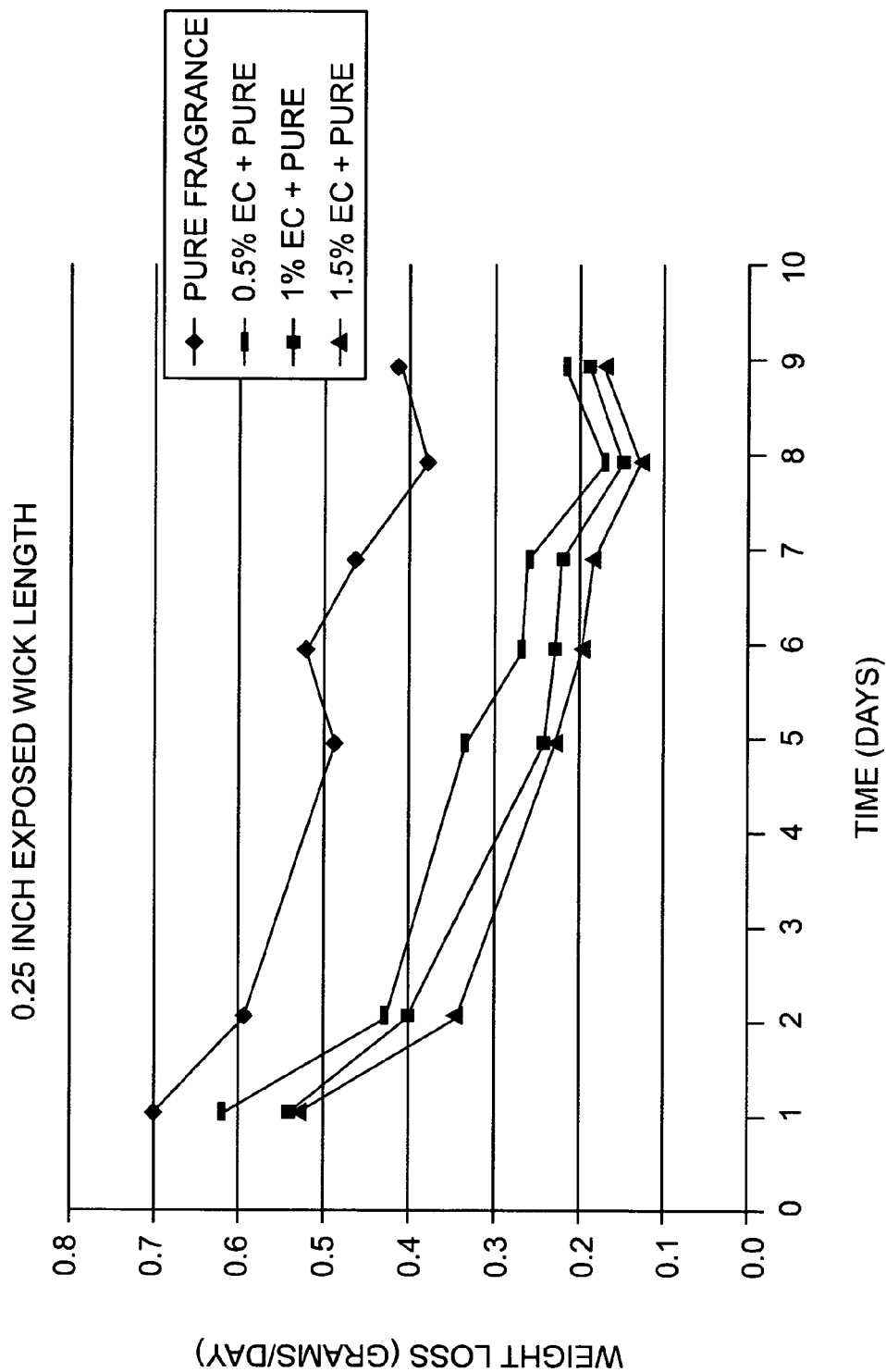
FIG. 5 is a graph showing the results of an evaporation test of wick-based devices.

The data from Table 2 are graphed in FIG. 5, which shows weight loss over time for fragrance mixtures and pure fragrance in bottles in which the wick of each bottle had an exposed wick length of 0.25 inches (0.635 cm). Comparison between the graph for pure fragrance and the graphs for the thickened fragrances reveals a reduction in the overall release rate for the bottles with the thickened fragrances, due to increases in viscosity caused by the addition of ethyl cellulose.

Table 3 shows data from this test for the set of PISO bottles with wicks having a 0.8 inch (2.032 cm) exposed wick length.

TABLE 3

Evaporation Test Results for 0.8 inch (2.032 cm) Exposed Wick Length

| elapsed time (days) | AVERAGE WEIGHT LOSS (grams/day) | | | |
|---|---|---|---|---|
|  | Pure Fragrance | 0.5% EC + pure fragrance | 1% EC + pure fragrance | 1.5% EC + pure fragrance |
| 1.01 | 1.901 | 1.777 | 1.575 | 1.425 |
| 2.01 | 1.507 | 1.150 | 1.054 | 0.913 |
| 3.05 | 1.303 | 0.995 | 0.741 | 0.692 |
| 4.95 | 1.101 | 0.796 | 0.627 | 0.511 |
| 5.95 | 0.892 | 0.535 | 0.473 | 0.465 |
| 6.94 | 0.939 | 0.631 | 0.513 | 0.410 |
| 7.98 | 0.681 | 0.430 | 0.328 | 0.298 |
| 8.98 | 0.783 | 0.490 | 0.408 | 0.378 |

Figure 6:
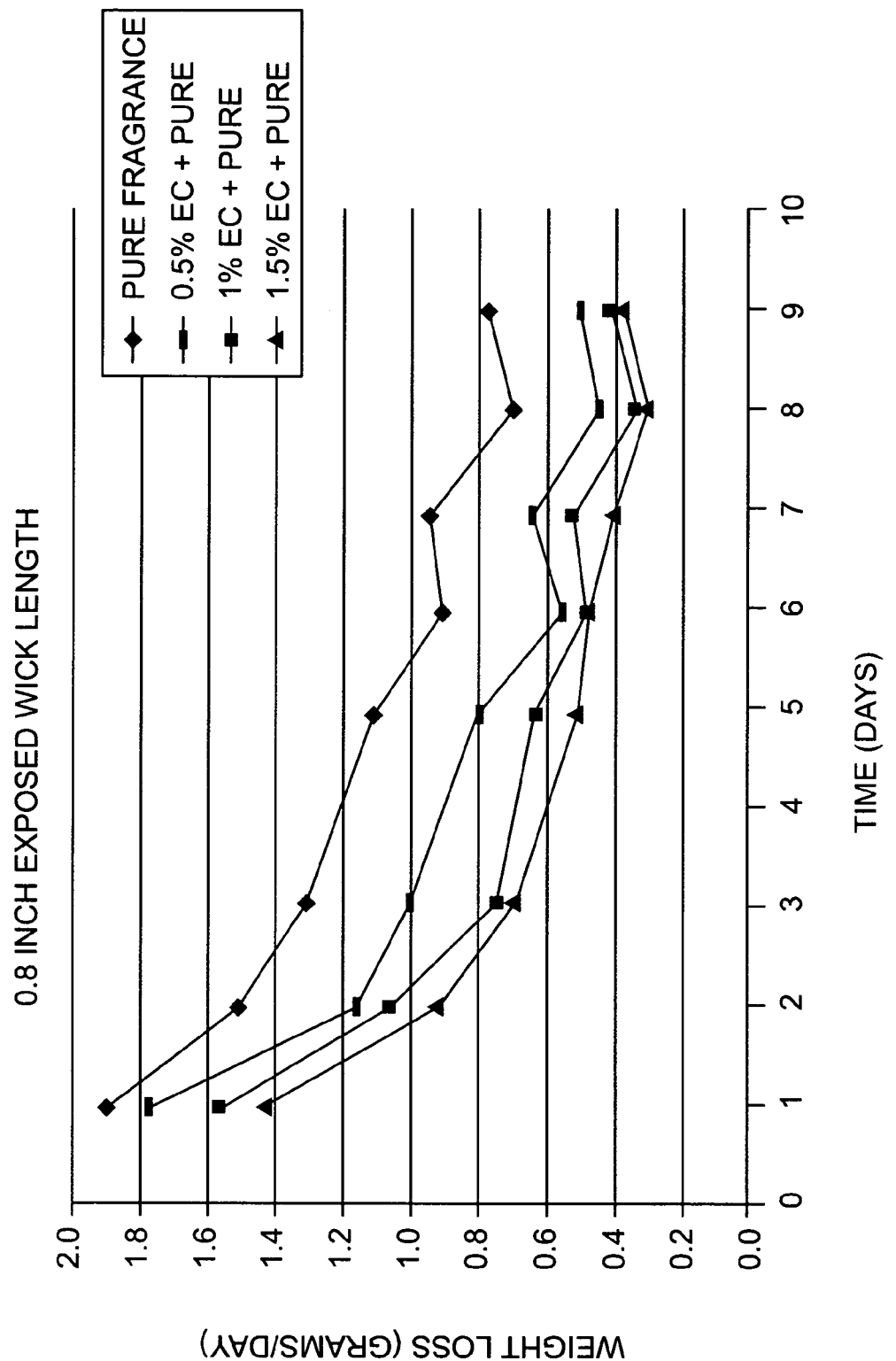
FIG. 6 is a graph showing the results of another evaporation test of wick-based devices.

The data from Table 3 are graphed in FIG. 6, which shows weight loss over time for fragrance mixtures and pure fragrance in bottles in which the wick of each bottle had an exposed wick length of 0.8 inches (2.032 cm). Comparison of FIG. 6 with FIG. 5 shows that the overall release rate in all of the bottles groups was increased due to the increase in the exposed surface area of the wick.

Example 3

Second Seepage Test

As discussed in section II, increasing the total surface area of the wick exposed to ambient air also increases the amount of seepage. This test demonstrates this result.

The following mixtures of ethyl cellulose and pure fragrance were filled into PISO bottles with vent holes and wicks with an exposed wick length of 0.8 inches (2.032 cm):
1) 0.5 wt % ethyl cellulose+pure fragrance
2) 1 wt % ethyl cellulose+pure fragrance
3) 1.5 wt % ethyl cellulose+pure fragrance.

Additional bottles were also filled with pure fragrance, as a control.

Each filled bottle was weighed for initial mass and then rested on its side with the wick touching a corrugated surface.

After twenty-four hours, each filled bottle was weighed again to find its final mass, and the amount of seepage (in grams/day) from each filled bottle was determined from the difference between its initial and final mass. Table 4 shows seepage test results from Example 1 (0.25 inch (0.635 cm) exposed wick length) alongside seepage test results from this example (0.8 inch (2.032 cm) exposed wick length).

TABLE 4

Seepage Test Results for 0.25 inch (0.635 cm) and 0.8 inch (2.032 cm) Exposed Wick Length

| composition | Seepage (g/day) | |
|---|---|---|
| | 0.25" (0.635 cm) exposed wick length | 0.8" (2.032 cm) exposed wick length |
| pure fragrance (control) | 2.571 | 7.011 |
| | 2.832 | 6.015 |
| | 2.515 | 6.024 |
| | 2.171 | |
| average | 2.522 | 6.35 |
| 0.5% Ethyl Cellulose + pure fragrance | 0.826 | 0.888 |
| | 0.675 | 0.794 |
| | 0.818 | 0.755 |
| average | 0.773 | 0.8123 |
| 1% Ethyl Cellulose + pure fragrance | 0.249 | 0.653 |
| | 0.288 | 0.667 |
| | 0.205 | 0.505 |
| | 0.237 | |
| average | 0.2448 | 0.6083 |
| 1.5% Ethyl Cellulose + pure fragrance | 0.207 | 0.256 |
| | 0.226 | 0.23 |
| | 0.127 | 0.291 |
| average: | 0.1867 | 0.259 |

Comparison of average seepage from bottles with a 0.25 inch (0.635 cm) exposed wick length with average seepage from bottles with a 0.8 inch (2.032 cm) exposed wick length shows that increasing the total surface area of the wick exposed to ambient air increased the amount of seepage from all corresponding groups of bottles. For example, in the 0.5 wt % ethyl cellulose-thickened fragrance group, average seepage increased from 0.773 g/day (0.25 inch (0.635 cm) exposed wick length) to 0.8123 g/day (0.8 inch (2.032 cm) exposed wick length).

Nevertheless, an increase in seepage within a group can represent a significant decrease in seepage across groups. This same 0.8123 g/day average seepage (from bottles filled with 0.5 wt % ethyl cellulose-thickened fragrance, and each having a wick of 0.8 inch (2.032 cm) exposed wick length) represents a nearly 68% reduction in seepage compared to the average seepage of 2.522 g/day from bottles filled with pure fragrance, and each having a wick of 0.25 inch (0.635 cm) exposed wick length.

Despite such a large reduction in average seepage across these two groups, the release rate for 0.5 wt % ethyl cellulose-thickened fragrance from wicks of 0.8 inch (2.032 cm) exposed wick length was significantly higher than the release rate for pure fragrance from wicks of 0.25 inch (0.635 cm) exposed wick length.

Example 4

Comparison of Evaporation Test Results

Table 5 reflects data gathered in Example 2. It shows average weight loss for pure fragrance in PISO bottles in which the wick of each bottle had a 0.25 inch (0.635 cm) exposed wick length, and b) 0.5 wt % ethyl cellulose+pure fragrance in PISO bottles in which the wick of each bottle had a 0.8 inch (2.032 cm) exposed wick length.

TABLE 5

Average Weight Loss (grams/day)

| a) 0.25 inch (0.635 cm) exposed wick length | | b) 0.8 inch (2.032 cm) exposed wick length | |
|---|---|---|---|
| elapsed time (days) | pure fragrance | elapsed time (days) | 0.5% EC + pure fragrance |
| 1.0 | 0.70166 | 1.01 | 1.777 |
| 2.1 | 0.59366 | 2.01 | 1.150 |
| 5.0 | 0.48694 | 3.05 | 0.995 |
| 6.0 | 0.52276 | 4.95 | 0.796 |
| 7.0 | 0.46376 | 5.95 | 0.535 |
| 8.0 | 0.38029 | 6.94 | 0.631 |
| 9.0 | 0.41243 | 7.98 | 0.430 |
| | | 8.98 | 0.490 |

Figure 7:
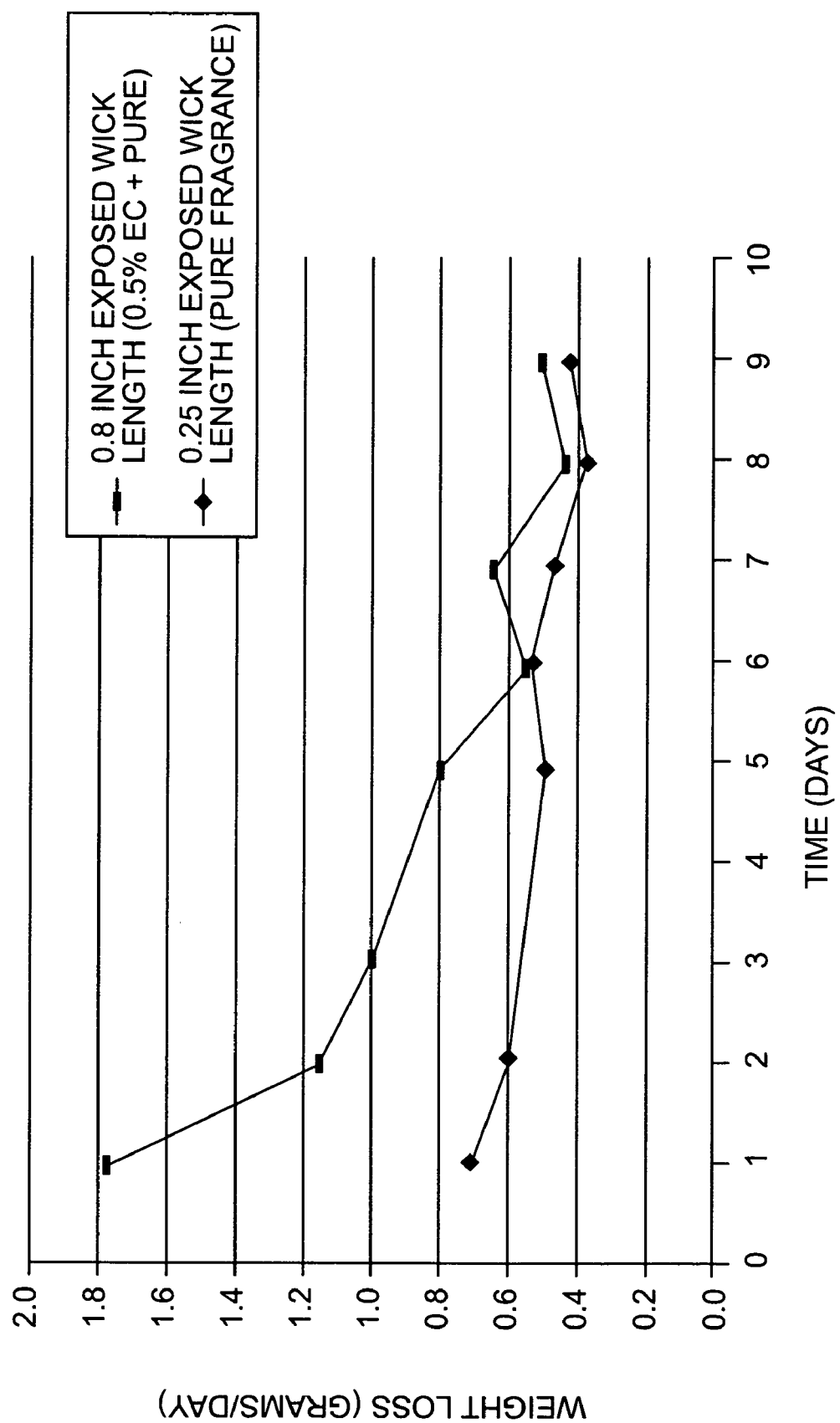
FIG. 7 is a graph comparing the results of evaporation tests of wick-based devices.

The numbers in Table 5 are graphed in FIG. 7, which shows the weight loss over time. Inspection of the two graphs shows that adding 0.5 wt % ethyl cellulose to pure fragrance and increasing the exposed length of the wick to 0.8 inches (2.032 cm) results in a release rate that is higher than the release rate of pure fragrance from a PISO bottle having a wick with a 0.25 inch (0.635 cm) exposed wick length over a nine-day period.

Therefore, by increasing the viscosity of the liquid (e.g., by adding ethyl cellulose) and increasing the exposed surface area of the wick (e.g., by increasing the length of the exposed part of the wick), seepage of the liquid can be reduced significantly while at the same time maintaining an acceptable release rate.

EXPERIMENT NO. 2

Example 5

Seepage Test

In this test, we examined the effect of increasing the viscosity of liquid inside the wick, but not the viscosity of liquid inside the bottle. Wicks having a 0.25 inch (0.635 cm) exposed wick length were first immersed in one of the following mixtures of ethyl cellulose and pure fragrance:

1) 1 wt % ethyl cellulose+pure fragrance 2) 2 wt % ethyl cellulose+pure fragrance 3) 3 wt % ethyl cellulose+pure fragrance.

Additional wicks were not pre-immersed in any liquid at all, as a control.

The wicks were placed inside PISO bottles having vent holes and containing pure fragrance. Each filled bottle was weighed for initial mass and then rested on its side with the wick touching a corrugated surface. After twenty-four hours, each filled bottle was weighed again to find its final mass, and the amount of seepage (in grams/day) from each filled bottle was determined from the difference between its initial and final mass. Table 6 shows seepage test results from bottles filled with pure fragrance and having either wicks saturated with thickened fragrance (pre-immersed) or wicks not saturated with any liquid (not pre-immersed).

TABLE 6

Seepage Test Results

| | seepage (g/day) | | | |
|---|---|---|---|---|
| | non-immersed wick (control) | 1% Ethyl Cellulose + pure fragrance | 2% Ethyl Cellulose + pure fragrance | 3% Ethyl Cellulose + pure fragrance |
| sample 1 | 2.645 | 0.147 | 0.025 | 0.018 |
| sample 2 | 5.703 | 0.121 | 0.033 | 0.056 |
| sample 3 | 5.642 | 0.131 | 0.024 | 0.016 |
| sample 4 | 5.843 | 0.063 | 0.193 | 0.017 |
| Average | 4.95825 | 0.1155 | 0.06875 | 0.02675 |

The results show reduced seepage from bottles with wicks saturated with thickened fragrance. Although pure fragrance was used inside all the bottles, immersing the wicks into the thickened fragrance could still reduce seepage from the wicks. This is because molecules of the thickened fragrance were absorbed in the walls of the wick pores, reducing the effective wick pore radius. This decrease in wick pore radius caused an increase in the flow resistance through the wick, resulting in a reduction in flow rate and a reduction in seepage from the wick.

V. Upper and Lower Limits of Viscosity

Having presented examples to illustrate why modifying the viscosity of liquid in wick-based devices is useful in reducing seepage, we turn to a discussion of a suitable range of viscosity to which the liquid may be brought.

We set the upper limit for viscosity by considering that the wicking rate of the liquid through the wick should be faster than the desired release rate of the vaporized liquid into the ambient air. When this condition is met, the liquid will rise from the liquid reservoir to an appropriate height within the wick at a rate fast enough not to diminish the overall release rate. The wicking rate of the liquid is influenced by the magnitude of driving capillary forces and resisting viscous forces.

The viscosity $\mu$ of the liquid should not exceed a value calculated according to the following:

$$\mu \leq \frac{A_{exp}\gamma R_p \varepsilon}{2(L+H_1)W}. \quad \text{(Equation 6)}$$

where W=desired release rate,
and as before,
$\varepsilon$=porosity of the wick,
$R_p$=radius of pores in the wick
$A_{exp}$=total surface area of the wick exposed to the ambient air,
L=length of portion of the wick outside the bottle 1 (see FIGS. 4A and 4B),
$H_1$=length of the portion of the wick inside the bottle 1 that is not submerged when the bottle 1 is right-side up (see FIG. 4A), and
$\gamma$=surface tension of the liquid.

We set the lower limit for viscosity by considering that the liquid should not seep or leak through the wick at an undesirable rate when the wick-based device is tilted such that a portion of the wick comes in contact with a different surface. In such a situation, the liquid can seep through due to gravity and capillary forces, especially if the contacted surface is porous. The seepage rate (the rate of flow at which liquid can flow through a media in the direction of gravity) is affected by the magnitude of driving gravitational forces and opposing viscous forces.

The viscosity $\mu$ of the liquid should be greater than a value calculated according to the following:

$$\mu \geq \frac{A_{exp}\rho g(L+H_2)R_p^2 \varepsilon}{100LS}. \quad \text{(Equation 7)}$$

where
S=seepage rate,
$\rho$=density of the liquid,
g=gravitational constant, and
$H_2$=length of portion of the wick inside the bottle 1 that is submerged when the bottle 1 is turned upside-down (see FIG. 4B),
and as before,
$\varepsilon$=porosity of the wick,
$R_p$=radius of pores in the wick,
$A_{exp}$=total surface area of the wick exposed to the ambient air, and
L=length of portion of the wick outside the bottle 1 (see FIGS. 4A and 4B).

In Tables 7 through 10, below, are numbers that were calculated based on Equations 6 and 7. The numbers were calculated with the following variables fixed:
$\rho$=1 gram/cm$^3$,
$\gamma$=25 g cm/s$^2$,
$H_1$=2 cm,
$H_2$=3 cm,
L=5 cm, and
$A_{exp}$=10 cm.

These are typical values of $\rho$, $\gamma$, $H_1$, $H_2$, L, and $A_{exp}$ for liquids and wicks used in wick-based devices. For the gravitational constant, we used the value g=980 cm/s$^2$.

A. Lower Limit of $\mu$, or Upper Limit of A/$\mu$L

With the above variables being fixed, the viscosity $\mu$ should be greater than or equal to the value calculated according to Equation 7, for different selected values of $R_p$ (radius of pores in the wick, in centimeters), $\varepsilon$ (porosity of the wick), and S (seepage rate, in grams/day). Table 7 shows the calculated values.

When the average pore size in a wick is about 1 to 2 microns ($R_p$=about 0.5 to 1 microns) or less, the influence of surface tension is much greater than the influence of liquid viscosity. Therefore, seepage is not as much a concern when the pore size is very small. Beginning at about 4 microns ($R_p$=about 2 microns), however, viscosity becomes an important factor, and seepage can be a problem. Therefore, in Table 7, the selected values of $R_p$ begin at 2 microns (0.0002 cm). All of the selected values of $R_p$ are typical values for the pore radius. As for $\varepsilon$, we selected two typical porosity values, 0.2 and 0.75. We have determined that an acceptable seepage value is about 1 gram per day, or less. Accordingly, for Table 7, we selected S values from 0.01 to 1 gram per day.

As Table 7 shows, in order to keep the seepage rate at about 1 gram per day, or less, in a wick-based device with a typical wick, the viscosity of liquid in the device should be at least about 0.11 poise (11 centipoise). For comparison, conventional fragrances have a viscosity of about 0.02 to 0.03 poise (about 2 to 3 centipoise).

We have found that it can often be difficult to measure the pore radius $R_p$ and porosity $\varepsilon$ of a wick, to ensure that increasing liquid viscosity to a particular minimum value will result in an acceptable seepage rate. However, the exposed surface area $A_{exp}$ and the length L of just about any wick are very easy to determine. Therefore, we have found the quantity $A_{exp}/\mu$L to be more useful than viscosity by itself.

Table 8 shows corresponding values of $A_{exp}/\mu L$ for the viscosity values in Table 7. As can be seen, to keep the seepage rate at an acceptable level of about 1 gram per day, or less, the upper limit for $A_{exp}/\mu L$ is about 18 cm/poise. Preferably, the upper limit for $A_{exp}/\mu L$ is about 9 cm/poise, which corresponds to a seepage rate of less than about 0.5 grams per day. Most preferably, the upper limit for $A_{exp}/\mu L$ is about 4 cm/poise, which corresponds to an excellent seepage rate of less than about 0.2 grams per day.

Naturally, even though the values selected for the variables in Equations 6 and 7 were typical values, not every wick will have, for example, a pore radius of 2 microns or a porosity of 0.75. Tables 7 and 8 do not represent rigid parameters that must be met, but rather are meant to illustrate a relationship between viscosity and $A_{exp}/\mu L$. In fact, an advantage of using $A_{exp}/\mu L$ is that it is accommodating of different pore radii and porosities, which can require more effort to measure and/or more cost to modify or achieve, whereas $A_{exp}$ and L are usually easier to determine, modify, and achieve. It is also worthwhile to note that $A_{exp}/\mu L$ nicely summarizes that seepage of liquid from a wick in a wick-based device can be controlled by adjusting the viscosity of the liquid in combination with adjusting the exposed surface area of the wick.

B. Upper Limit of $\mu$, or Lower Limit of $A/\mu L$

As mentioned previously, the upper limit for viscosity is set by the criterion that the wicking rate of the liquid through the wick should be faster than the desired release rate of the vaporized liquid into the ambient air.

For $\rho=1$ gram/cm$^3$, $\gamma=25$ g cm/s$^2$, $H_1=2$ cm, $L=5$ cm, $A_{exp}=10$ cm$^2$, and g=980 cm/s$^2$, as above, the maximum viscosity $\mu$ is calculated according to Equation 6, for different selected values of $R_p$ (radius of pores in the wick, in centimeters), $\epsilon$ (porosity of the wick), and W (release rate, in grams/day). Table 9 shows the calculated maximum values of the viscosity $\mu$.

As in Tables 7 and 8, selected typical values of $R_p$ begin at 2 microns (0.0002 cm). Typical values of porosity $\epsilon$, 0.2 and 0.75, were again used. As for desired release rate W of the liquid, we have determined that a desired value is about 1 gram per day, or more. Accordingly, for Table 9, we selected W values from 1 to 2 grams per day.

As Table 9 shows, in order to keep the release rate at about 1 gram per day, or more, in a wick-based device with a typical wick, the viscosity of liquid in the device should be no more than about 2,893 poise. Although the viscosity can be

TABLE 7

Values of μ for various wick pore radii, porosities, and seepage rates

| | $R_p$ (cm) | | | | | | | |
|---|---|---|---|---|---|---|---|---|
| | 0.0002 | 0.0005 | 0.001 | 0.0025 | 0.0002 | 0.0005 | 0.001 | 0.0025 |
| | | | | $\epsilon$ | | | | |
| S (g/day) | 0.2 μ (poise) | 0.2 μ (poise) | 0.2 μ (poise) | 0.2 μ (poise) | 0.75 μ (poise) | 0.75 μ (poise) | 0.75 μ (poise) | 0.75 μ (poise) |
| 0.01 | 10.84 | 67.74 | 270.95 | 1693.44 | 40.64 | 254.02 | 1016.06 | 6350.40 |
| 0.1 | 1.08 | 6.77 | 27.10 | 169.34 | 4.06 | 25.40 | 101.61 | 635.04 |
| 0.2 | 0.54 | 3.39 | 13.55 | 84.67 | 2.03 | 12.70 | 50.80 | 317.52 |
| 0.3 | 0.36 | 2.26 | 9.03 | 56.45 | 1.35 | 8.47 | 33.87 | 211.68 |
| 0.4 | 0.27 | 1.69 | 6.77 | 42.34 | 1.02 | 6.35 | 25.40 | 158.76 |
| 0.5 | 0.22 | 1.35 | 5.42 | 33.87 | 0.81 | 5.08 | 20.32 | 127.01 |
| 0.6 | 0.18 | 1.13 | 4.52 | 28.22 | 0.68 | 4.23 | 16.93 | 105.84 |
| 0.7 | 0.15 | 0.97 | 3.87 | 24.19 | 0.58 | 3.63 | 14.52 | 90.72 |
| 0.8 | 0.14 | 0.85 | 3.39 | 21.17 | 0.51 | 3.18 | 12.70 | 79.38 |
| 0.9 | 0.12 | 0.75 | 3.01 | 18.82 | 0.45 | 2.82 | 11.29 | 70.56 |
| 1 | 0.11 | 0.68 | 2.71 | 16.93 | 0.41 | 2.54 | 10.16 | 63.50 |

TABLE 8

Values of A/μL for various wick pore radii, porosities, and seepage rates

| | $R_p$ (cm) | | | | | | | |
|---|---|---|---|---|---|---|---|---|
| | 0.0002 | 0.0005 | 0.001 | 0.0025 | 0.0002 | 0.0005 | 0.001 | 0.0025 |
| | | | | $\epsilon$ | | | | |
| S (g/day) | 0.2 A/(μL) | 0.2 A/(μL) | 0.2 A/(μL) | 0.2 A/(μL) | 0.75 A/(μL) | 0.75 A/(μL) | 0.75 A/(μL) | 0.75 A/(μL) |
| 0.01 | 0.18 | 0.03 | 0.01 | 0.00 | 0.05 | 0.01 | 0.00 | 0.00 |
| 0.1 | 1.85 | 0.30 | 0.07 | 0.01 | 0.49 | 0.08 | 0.02 | 0.00 |
| 0.2 | 3.69 | 0.59 | 0.15 | 0.02 | 0.98 | 0.16 | 0.04 | 0.01 |
| 0.3 | 5.54 | 0.89 | 0.22 | 0.04 | 1.48 | 0.24 | 0.06 | 0.01 |
| 0.4 | 7.38 | 1.18 | 0.30 | 0.05 | 1.97 | 0.31 | 0.08 | 0.01 |
| 0.5 | 9.23 | 1.48 | 0.37 | 0.06 | 2.46 | 0.39 | 0.10 | 0.02 |
| 0.6 | 11.07 | 1.77 | 0.44 | 0.07 | 2.95 | 0.47 | 0.12 | 0.02 |
| 0.7 | 12.92 | 2.07 | 0.52 | 0.08 | 3.44 | 0.55 | 0.14 | 0.02 |
| 0.8 | 14.76 | 2.36 | 0.59 | 0.09 | 3.94 | 0.63 | 0.16 | 0.03 |
| 0.9 | 16.61 | 2.66 | 0.66 | 0.11 | 4.43 | 0.71 | 0.18 | 0.03 |
| 1 | 18.45 | 2.95 | 0.74 | 0.12 | 4.92 | 0.79 | 0.20 | 0.03 | adjusted to exceed that value, doing so would bring the release rate W to below the desired value of about 1 gram per day.

Table 10 shows corresponding values of $A_{exp}/\mu L$ for the viscosity values in Table 9. Again, we have found the quantity $A_{exp}/\mu L$ to be more useful than viscosity by itself, since it can often be difficult to measure the pore radius $R_p$ and porosity $\epsilon$ of a wick, to ensure that increasing the liquid viscosity to a particular value (to reduce seepage) will not result in an unacceptably low release rate. However, as mentioned previously, the exposed surface area $A_{exp}$ and the length L of just about any wick are very easy to determine.

As can be seen in Table 10, to keep the release rate at a desired level of about 1 gram per day, or more, the lower limit for $A_{exp}/\mu L$ is about $4 \times 10^{-4}$ cm/poise.

Again, even though the values selected for the variables in Equations 6 and 7 were typical values, not every wick will have, for example, a pore radius of 2 microns or a porosity of 0.75. Therefore, like Tables 7 and 8, Tables 9 and 10 do not represent rigid parameters that must be met, but rather are meant to illustrate a relationship between viscosity and $A_{exp}/\mu L$. Using $A_{exp}/\mu L$ is advantageous because it is accommodating of different pore radii and porosities and because $A_{exp}$ and L are usually easier to determine, modify, and achieve.

Range of $A_{exp}/\mu L$

As this section has explained, the seepage of liquid from a wick in a wick-based device can be controlled by adjusting the viscosity of the liquid in combination with adjusting the exposed surface area of the wick such that $A_{exp}/\mu L$ is within a certain range. This range is from about $4 \times 10^{-4}$ to about 18 cm/poise, preferably from about $4 \times 10^{-4}$ to about 9 cm/poise, and most preferably from about $4 \times 10^{-4}$ to about 4 cm/poise. The upper limit of $A_{exp}/\mu L$ is set so that the seepage rate will be at or below an acceptable level, while the lower limit of $A_{exp}/\mu L$ is set so that the release rate will still be at or above a desired level. In this way, seepage can be reduced in wick-based devices that maintain good performance.

TABLE 9

Values of $\mu$ for various wick pore radii, porosities, and seepage rates

| | $R_p$ (cm) | | | | | | | |
|---|---|---|---|---|---|---|---|---|
| | 0.0002 | 0.0005 | 0.001 | 0.0025 | 0.0002 | 0.0005 | 0.001 | 0.0025 |
| | $\epsilon$ | | | | | | | |
| | 0.2 | 0.2 | 0.2 | 0.2 | 0.75 | 0.75 | 0.75 | 0.75 |
| W (g/d) | μ (poise) | μ (poise) | μ (poise) | μ (poise) | μ (poise) | μ (poise) | μ (poise) | μ (poise) |
| 1.0 | 61.7 | 154.3 | 308.6 | 771.4 | 231.4 | 578.6 | 1157.1 | 2892.9 |
| 1.1 | 56.1 | 140.3 | 280.5 | 701.3 | 210.4 | 526.0 | 1051.9 | 2629.9 |
| 1.2 | 51.4 | 128.6 | 257.1 | 642.9 | 192.9 | 482.1 | 964.3 | 2410.7 |
| 1.3 | 47.5 | 118.7 | 237.4 | 593.4 | 178.0 | 445.1 | 890.1 | 2225.3 |
| 1.4 | 44.1 | 110.2 | 220.4 | 551.0 | 165.3 | 413.3 | 826.5 | 2066.3 |
| 1.5 | 41.1 | 102.9 | 205.7 | 514.3 | 154.3 | 385.7 | 771.4 | 1928.6 |
| 1.6 | 38.6 | 96.4 | 192.9 | 482.1 | 144.6 | 361.6 | 723.2 | 1808.0 |
| 1.7 | 36.3 | 90.8 | 181.5 | 453.8 | 136.1 | 340.3 | 680.7 | 1701.7 |
| 1.8 | 34.3 | 85.7 | 171.4 | 428.6 | 128.6 | 321.4 | 642.9 | 1607.1 |
| 1.9 | 32.5 | 81.2 | 162.4 | 406.0 | 121.8 | 304.5 | 609.0 | 1522.6 |
| 2.0 | 30.9 | 77.1 | 154.3 | 385.7 | 115.7 | 289.3 | 578.6 | 1446.4 |

TABLE 10

Values of $A/\mu L$ for various wick pore radii, porosities, and seepage rates

| | $R_p$ (cm) | | | | | | | |
|---|---|---|---|---|---|---|---|---|
| | 0.0002 | 0.0005 | 0.001 | 0.0025 | 0.0002 | 0.0005 | 0.001 | 0.0025 |
| | $\epsilon$ | | | | | | | |
| | 0.2 | 0.2 | 0.2 | 0.2 | 0.75 | 0.75 | 0.75 | 0.75 |
| W (g/d) | A/(μL) | A/(μL) | A/(μL) | A/(μL) | A/(μL) | A/(μL) | A/(μL) | A/(μL) |
| 1.0 | 0.0165 | 0.0066 | 0.0033 | 0.0013 | 0.0044 | 0.0018 | 0.0009 | 0.0004 |
| 1.1 | 0.0182 | 0.0073 | 0.0036 | 0.0015 | 0.0049 | 0.0019 | 0.0010 | 0.0004 |
| 1.2 | 0.0198 | 0.0079 | 0.0040 | 0.0016 | 0.0053 | 0.0021 | 0.0011 | 0.0004 |
| 1.3 | 0.0215 | 0.0086 | 0.0043 | 0.0017 | 0.0057 | 0.0023 | 0.0011 | 0.0005 |
| 1.4 | 0.0231 | 0.0093 | 0.0046 | 0.0019 | 0.0062 | 0.0025 | 0.0012 | 0.0005 |
| 1.5 | 0.0248 | 0.0099 | 0.0050 | 0.0020 | 0.0066 | 0.0026 | 0.0013 | 0.0005 |
| 1.6 | 0.0265 | 0.0106 | 0.0053 | 0.0021 | 0.0071 | 0.0028 | 0.0014 | 0.0006 |
| 1.7 | 0.0281 | 0.0112 | 0.0056 | 0.0022 | 0.0075 | 0.0030 | 0.0015 | 0.0006 |
| 1.8 | 0.0298 | 0.0119 | 0.0060 | 0.0024 | 0.0079 | 0.0032 | 0.0016 | 0.0006 |
| 1.9 | 0.0314 | 0.0126 | 0.0063 | 0.0025 | 0.0084 | 0.0034 | 0.0017 | 0.0007 |
| 2.0 | 0.0331 | 0.0132 | 0.0066 | 0.0026 | 0.0088 | 0.0035 | 0.0018 | 0.0007 |

INDUSTRIAL APPLICABILITY

This invention provides methods for reducing seepage from a wick-based controlled release device for transporting liquids from a reservoir to a surface exposed to the ambient air. The invention also provides wick-based controlled release devices, with reduced seepage, for transporting liquids from a reservoir to a surface exposed to the ambient air. We envision that the devices preferably can be used, and the methods preferably can be applied, for example, to dispense fragrances, insecticides, and any other vaporizable materials into the ambient air to freshen or deodorize the air or to exterminate airborne pests.

While particular embodiments of the present invention have been illustrated and described, it will be apparent to those skilled in the art that various changes and modifications may be made without departing from the spirit and scope of the invention. Furthermore, it is intended that the claims will cover all such modifications that are within the scope of the invention.

We claim:

1. A method of reducing seepage of liquid from a wick-based device having a porous wick, the wick having pores with pore walls, and a container for holding a first liquid having a first viscosity, the method comprising:
   providing a second liquid having a second viscosity greater than the first viscosity, the second liquid being able to be absorbed into the pore walls in the wick and to decrease the effective size of the pores; and
   applying the second liquid to the wick such that at least a portion of the wick is saturated with the second liquid, so as to reduce seepage of the first liquid from the wick-based device,
   wherein the first liquid comprises a fragrance or an insect repellant to be released from the wick-based device.

2. The method of claim 1, wherein the second liquid comprises a polymeric thickener.

3. The method of claim 2, wherein the polymeric thickener is ethyl cellulose.

4. The method of claim 1, wherein the second liquid comprises an emulsifier.

5. A method of reducing seepage of liquid from a wick-based device having a container having a liquid with a viscosity g, and a porous wick with an average pore size of about 4 microns to about 50 microns and a porosity $\epsilon$ between about 0.20 to about 0.75, and having a length L and a total exposed surface area A exposed to the ambient air, the method comprising: adjusting the viscosity g of the liquid, the length L of the wick, and the total exposed surface area A of the wick such that a quantity $A/\mu L$ is in a range of about $4 \times 10{-4}$ to about 18 cm/poise, so as to reduce seepage of the liquid from the wick-based device.

6. The method of claim 5, wherein said adjusting step comprises adding a thickener to the liquid.

7. The method of claim 6, wherein the thickener is ethyl cellulose.

8. The method of claim 5, wherein the quantity $A/\mu L$ is in a range of about $4 \times 10^{-4}$ to about 4 cm/poise.

9. The method of claim 5, wherein the liquid comprises an emulsifier.

10. The method of claim 9, wherein the emulsifier is sorbitan monooleate.

11. A wick-based device comprising: a container having a liquid with a viscosity g; and a porous wick with an average pore size of about 4 microns to about 50 microns and a porosity $\epsilon$ between about 0.20 to about 0.75, and having a length L and a total exposed surface area A exposed to the ambient air, wherein the viscosity g of the liquid, the length L of the wick, and the total exposed surface area A of the wick are adjusted such that a quantity $A/\mu L$ is in a range of about $4 \times 10{-4}$ to about 18 cm/poise.

12. The device of claim 11, wherein the liquid comprises an emulsifier.

13. The device of claim 12, wherein the emulsifier is sorbitan monooleate.

14. The device of claim 11, wherein said container has a vent hole.

15. The device of claim 11, wherein the quantity $A/\mu L$ is in a range of about $4 \times 10^{-4}$ to about 4 cm/poise.

16. The device of claim 11, wherein the liquid comprises a thickener.

17. The device of claim 16, wherein the thickener is ethyl cellulose.

* * * * *